United States Patent [19]
Herbert et al.

[11] Patent Number: 6,153,129
[45] Date of Patent: *Nov. 28, 2000

[54] PRODUCTION SCALE METHOD OF FORMING MICROPARTICLES

[75] Inventors: Paul F. Herbert, Wayland; Michael S. Healy, East Bridgewater, both of Mass.

[73] Assignee: Alkermes Controlled Therapeutics, Inc., Cambridge, Mass.

[*] Notice: This patent is subject to a terminal disclaimer.

[21] Appl. No.: 09/305,413

[22] Filed: May 5, 1999

Related U.S. Application Data

[63] Continuation of application No. 08/443,726, May 18, 1995, Pat. No. 5,922,253.

[51] Int. Cl.$^7$ .................................................. B29B 9/02
[52] U.S. Cl. .................................................. 264/5; 264/13
[58] Field of Search ............................................ 264/5, 13

[56] References Cited

U.S. PATENT DOCUMENTS

| | | | |
|---|---|---|---|
| 3,523,906 | 8/1970 | Vrancken et al. | 252/316 |
| 3,691,090 | 9/1972 | Kitajima et al. | 252/316 |
| 3,737,337 | 6/1973 | Schmoring et al. | 117/100 |
| 3,887,699 | 6/1975 | Yolles | 424/19 |
| 3,891,570 | 6/1975 | Fukushima et al. | 252/316 |
| 3,928,566 | 12/1975 | Briggs et al. | 424/94 |
| 4,166,800 | 9/1979 | Fong | 252/316 |
| 4,389,330 | 6/1983 | Tice et al. | 427/213.36 |
| 4,530,840 | 7/1985 | Tice et al. | 514/179 |
| 4,542,025 | 9/1985 | Tice et al. | 424/78 |
| 4,675,189 | 6/1987 | Kent et al. | 424/490 |
| 4,804,741 | 2/1989 | Verbiscar et al. | 528/931 |
| 4,835,139 | 5/1989 | Tice et al. | 514/15 |
| 5,019,400 | 5/1991 | Gombotz et al. | 424/497 |
| 5,192,741 | 3/1993 | Orsolini et al. | 514/4 |
| 5,922,253 | 7/1999 | Herbert et al. | 264/5 |

FOREIGN PATENT DOCUMENTS

| | | |
|---|---|---|
| WO 89/03678 | 5/1989 | WIPO . |
| WO 90/13285 | 11/1990 | WIPO . |
| WO 90/13780 | 11/1990 | WIPO . |
| WO 93/07861 | 4/1993 | WIPO . |

OTHER PUBLICATIONS

Santo, Toyomi, et al., "Porous Biodegradable Microspheres for Controlled Drug Delivery. I. Assessment of Processing Conditions and Solvent Removal Techniques," *Pharmaceutical Research*, 5(1): 21–29 (1988).

*Primary Examiner*—Jeffrey C. Mullis
*Attorney, Agent, or Firm*—Hamilton, Brook, Smith & Reynolds, P.C.

[57] ABSTRACT

The present invention relates to a method for forming microparticles of a material from microdroplets of a solution, wherein the solution comprises the material dissolved in a solvent. The method includes the steps of directing the microdroplets into a freezing zone, wherein the freezing zone is surrounded by a liquified gas, and wherein the microdroplets freeze. The frozen microdroplets are then mixed with a liquid non-solvent, whereby the solvent is extracted into the non-solvent, thereby forming the microparticles.

22 Claims, 4 Drawing Sheets

PRODUCTION SCALE METHOD OF FORMING MICROPARTICLES

RELATED APPLICATIONS

This application is a Continuation of U.S. patent application Ser. No. 08/443,726, filed on May 18, 1995, now U.S. Pat. No. 5,922,253 the entire teachings of which are incorporated herein by reference.

BACKGROUND OF THE INVENTION

Many illnesses or conditions require a constant level of medicaments or agents in vivo to provide the most effective prophylactic, therapeutic or diagnostic results. In the past, medicaments were given in doses at intervals which resulted in fluctuating medication levels.

Attempts to control and steady medication levels have more recently included the use of many biodegradable substances, such as polymeric and protein microspheres containing the medicament. The use of these microspheres provided an improvement in the controlled release of medicaments by utilizing the inherent biodegradability of the polymer to improve the release of the medicament and provide a more even, controlled level of medication.

However, many of these methods result in low yields of microspheres due to a combination of the methods and apparatus used. Further, some processes cannot be scaled-up from experimental level to a commercial production level.

Therefore, a need exists for a method of forming microspheres with lower losses of biologically active agent, high product yields, and commercial-scale feasibility.

SUMMARY OF THE INVENTION

This invention relates to a method for forming microparticles of a material from microdroplets of a solution, wherein the solution comprises the material dissolved in a solvent. The method includes the steps of directing the microdroplets into a freezing zone, wherein the freezing zone is surrounded by a liquified gas, and wherein the microdroplets freeze. The frozen microdroplets are then mixed with a liquid non-solvent, whereby the solvent is then extracted into the non-solvent, thereby forming the microparticles.

This invention has numerous advantages, for instance, this method and apparatus provides high yields, commercial production levels of controlled release microparticles, an enclosed system for aseptic processing, microparticle size control and process control reproducibility In addition, the method of invention permits greater tailoring of temperature profiles during performance of the method.

Figure 1:
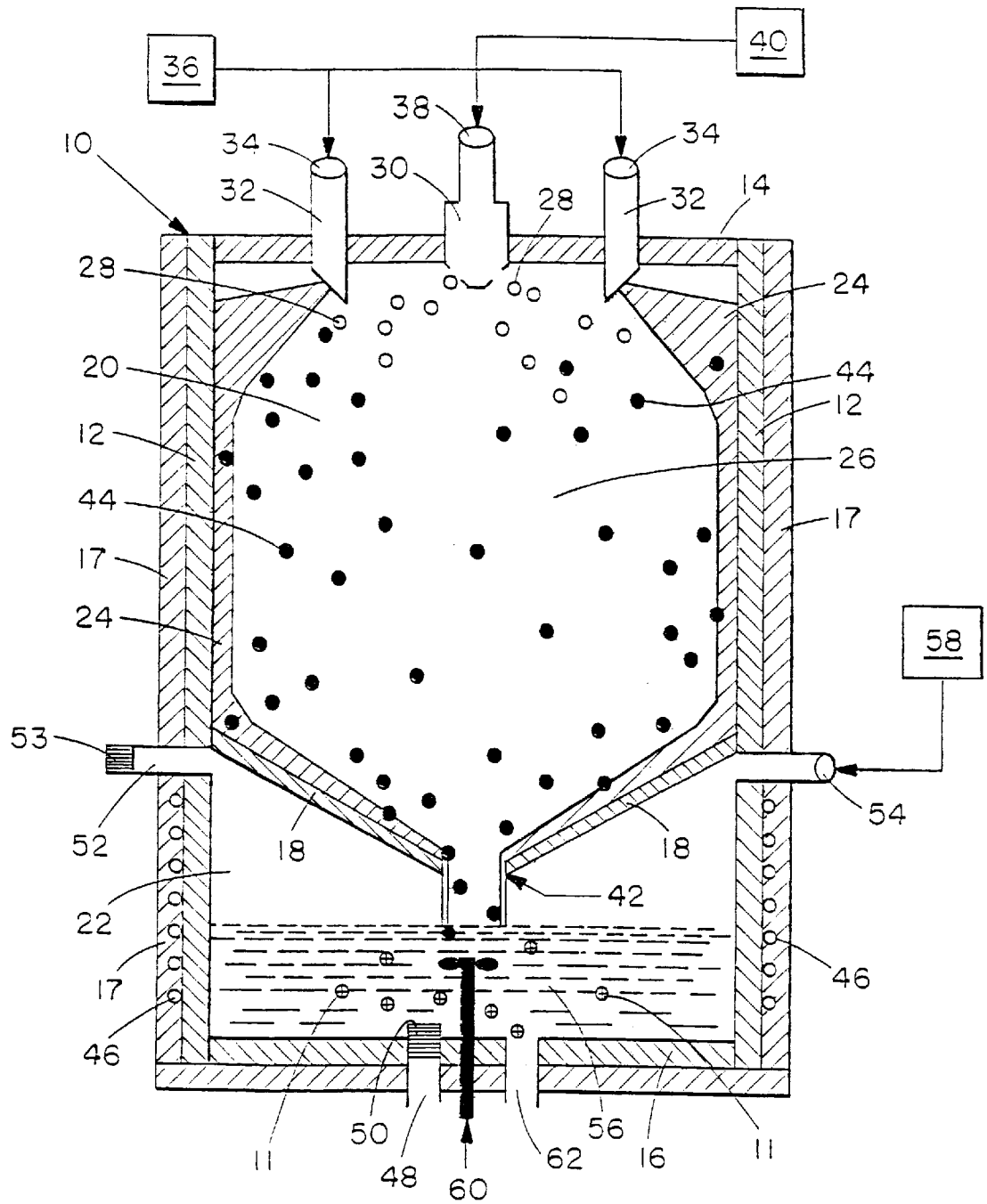
FIG. 1 is a cut-away side elevational illustration of an apparatus of the invention suitable for forming microparticles of a material, according to the method of the invention by freezing microdroplets of a solution of the material in a solvent, within a freezing zone cooled by an encircling flow of liquified gas and then extracting the solvent from the frozen microdroplets, by exposure to a liquid non-solvent.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

The features and other details of the apparatus and method of the invention, will now be more particularly described with reference to the accompanying drawings and pointed out in the claims. It is understood that the particular embodiments of the invention are shown by way of illustration and not as limitations of the invention. The principle features of this invention can be employed in various embodiments without departing from the scope of the invention.

The present invention relates to a method and apparatus for forming microparticles of a material from a solution of the material. A microparticle, as defined herein, comprises a particle of a material having a diameter of less than about one millimeter. A microparticle can have a spherical, non-spherical or irregular shape. It is preferred that a microparticle be a microsphere.

Materials suitable to form microparticles of this invention include, for example, polymers, peptides, polypeptides, proteins, small molecule drugs and pro-drugs.

A microparticle can also contain one or more additional substance, which is dispersed within the microparticle. Wherein the material comprises a polymer, the polymer solution contains at least one biologically active agent.

A biologically active agent, as defined herein, is an agent, or a metabolite of the agent, which possesses therapeutic, prophylactic or diagnostic properties in vivo, in the form of said agent when administered, or after metabolism (e.g., a pro-drug, such as hydrocortisone succinate).

One embodiment of an apparatus of the invention, suitable for performing the method of invention, is illustrated in FIG. 1. Said apparatus includes vessel 10, typically in a cylindrical shape, having side wall 12, vessel top 14, vessel bottom 16 and internal wall 18. Side wall 12 and vessel bottom 16 are usually insulated, using conventional insulation methods, to minimize heat leakage from the outside environment into vessel 10, thereby providing improved temperature control within vessel 10. Conventional insulation methods include, for example, application of at least one layer of insulation material 17 to cover the outside surfaces of side wall 12 and vessel bottom 16. Other means of insulating include, for instance, vacuum jacketing side wall 12 and vessel bottom 16 with radiation shielding. Suitable insulation materials include conventional insulation materials, such as mineral fiber, polystyrene, polyurethane, rubber foams, balsa wood or corkboard.

In this embodiment, vessel top 14 is typically not insulated, thereby allowing components of said apparatus, disposed at or near vessel top 14, to be warmed by heat leakage into the vessel 10. Alternately, vessel top 14 may also be insulated with a suitable insulation material.

Vessel 10 is fabricated with a material which can withstand conditions during steam sanitizing, of the inside of vessel 10, and can also withstand the temperatures and gas pressures experienced in vessel 10 while performing the method of invention for forming microparticles 11. Suitable materials for vessel 10 include, for example, stainless steel, polypropylene and glass.

Vessel 10, in this embodiment, is a single unitary vessel, divided into freezing section 20 and extraction section 22. Freezing section 20 is disposed within, and substantially enclosed by, side wall 12, vessel top 14 and internal wall 18. Extraction section 22 is disposed within, and substantially enclosed by, side wall 12, vessel bottom 16 and internal wall 18.

In an alternate embodiment, freezing section 20 and extraction section 22 comprises separate vessels, wherein the freezing section vessel is disposed generally above the extraction section vessel, and wherein the bottom of the freezing section vessel is connected to the top or to a side of the extraction section vessel.

Vessel 10 also includes means for directing liquified gas into freezing section 20 to form liquified gas flow 24. Liquified gas flow 24 consists of a spray of liquified gas and/or at least one stream of liquified gas. Liquified gas flow 24 begins in freezing section 20 at or near vessel top 14, and then runs in a generally downward direction, toward internal wall 18. Within freezing section 20, at least a portion of liquified gas flow 24 runs substantially parallel with side wall 12. Liquified gas flow 24 is typically disposed at or near side wall 12. It is preferred that side wall 12 is generally wetted by liquified gas flow 24. Furthermore, liquified gas flow 24 substantially encircles freezing zone 26, which is approximately disposed about the radial centerline of freezing section 20. The extent to which liquified gas flow 24 has gaps in the encircling flow about freezing zone 26, is dependent upon the type and number of liquified gas directing means employed.

At least one suitable liquified gas directing means is disposed at or near vessel top 14, at a location which is radially displaced from the center of vessel top 14. The radial displacement of a liquified gas directing means, is sufficient if the liquified gas directing means does not significantly interfere with the formation of microdroplets 28, such as by freezing a portion of a solution from which microdroplets 28 are formed at microdroplet forming means 30, thereby at least partially clogging microdroplet forming means 30. A liquified gas directing means can also interfere if a significant portion of microdroplets 28 impact said liquified gas directing means.

In the embodiment illustrated in FIG. 1, suitable liquified gas directing means include at least two spray nozzles 32 having a line discharge or preferably a fan discharge (e.g., flood jet atomizer model 1/8-K-SS-1, operated with a liquid gas pressure of about 20 psig; Spray Systems Co., Wheaton, Ill.), which are capable of spraying a liquified gas to form at least a portion of liquified gas flow 24. Spray nozzles 32 are disposed in freezing section 20 at vessel top 14, and are about equidistantly spaced at positions approximately located on a circle centered around the center of vessel top 14, or centered around microdroplet forming means 30 if radially displaced from said vessel top center. The number of spray nozzles 32 used will depend upon the arc of the nozzle discharge and the distance from nozzle 32 to the impact point on side wall 12 of liquified gas flow 24.

With two spray nozzles 32 equidistantly displaced from the center of the top of freezing section 20, encircling liquified gas flow 24 will typically have two gaps about 180° apart, due to the usual inability of spray nozzle 32 to spray in greater than a 180° arc. In a preferred embodiment, at least three spray nozzles are disposed in freezing section 20 to form liquified gas flow 24 which encircles freezing zone 26 typically without any significant gaps in the encircling flow.

Typically, three spray nozzles 32, equidistantly spaced will provide a 360° liquified gas flow 24. In a more preferred embodiment, six spray nozzles are equidistantly disposed about the center of freezing section 20.

A liquified gas directing means receives liquified gas, from at least one liquified gas inlet 34. Liquified gas inlet 34 provides fluid communication between liquified gas source 36 and the liquified gas directing means. It is understood that other suitable liquified gas introduction means, capable of directing liquified gas flow into the liquified gas directing means, can be used in place of, or in combination with, liquified gas inlet 34.

Figure 2:
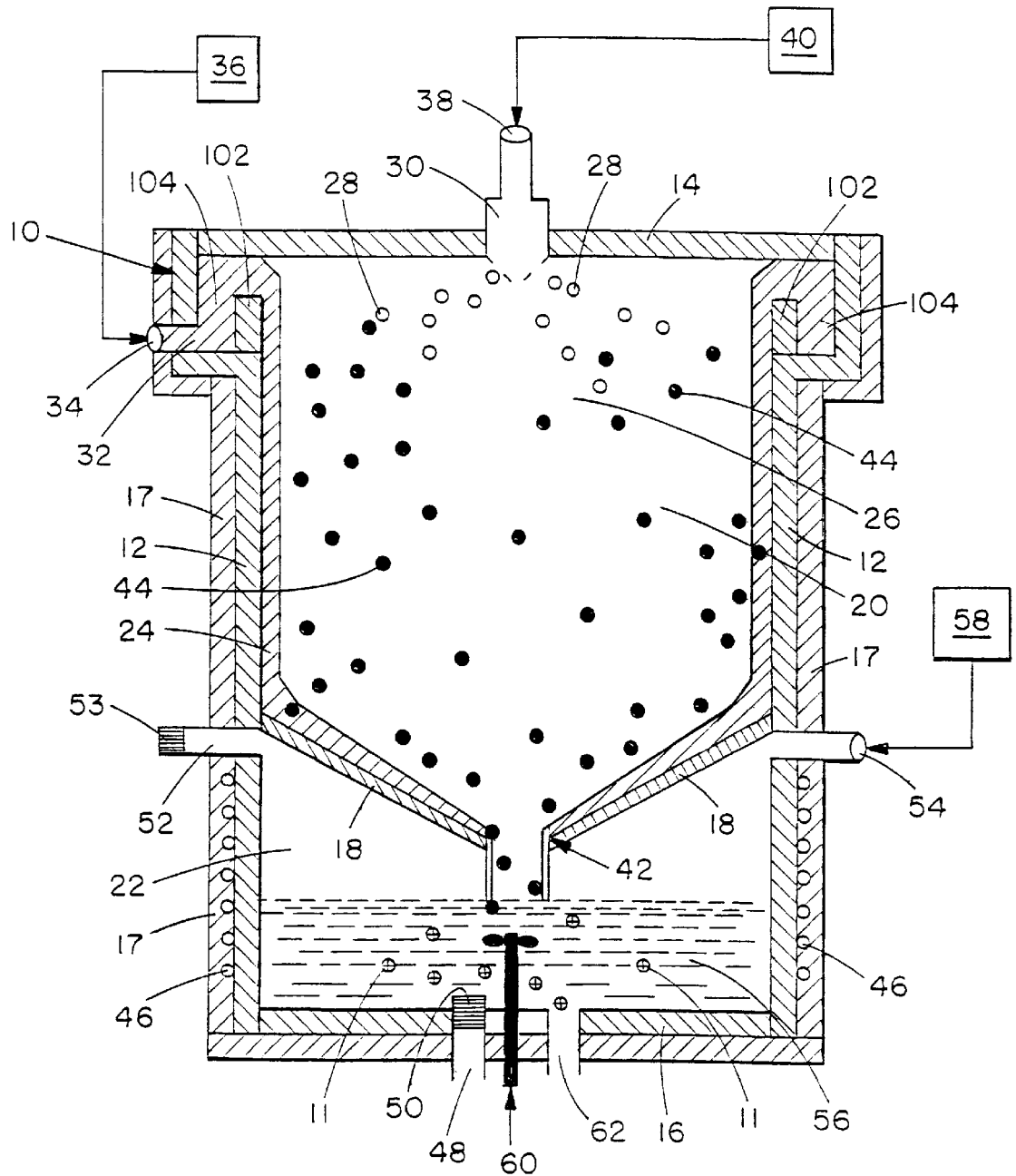
FIG. 2 is a cut-away side elevational illustration of another embodiment of an apparatus of the invention suitable for forming microparticles of a material according to the method of the invention, by freezing microdroplets of a solution of the material in a solvent, within a freezing zone cooled by an encircling flow of a liquified gas and then extracting the solvent from the frozen microdroplets, by exposure to a liquid non-solvent.

FIG. 2 illustrates another embodiment of a suitable liquified gas directing means of an apparatus of this invention. The apparatus of FIG. 2 has many of the same elements of FIG. 1 and like elements are designated with like numerals. In said apparatus, suitable liquified gas directing means comprises weir 102 and liquified gas space 104. Weir 102 is disposed within freezing section 20, between side wall 12 and freezing zone 26. Weir 102 extends from internal wall 18, or alternately from side wall 12, and extends upwards toward vessel top 14. In one embodiment, the top portion of weir 102 does not contact vessel top 14, thus permitting liquified gas to flow over the top of weir 102 and further into freezing section 20. Alternately, wherein weir 102 contacts vessel top 14, weir 102 is porous or slotted at the top of weir 102 (not shown) to permit liquified gas to flow through the top section of weir 102, and further into freezing section 20.

Liquified gas space 104 is disposed within freezing section 20, between weir 102 and side wall 12. Liquified gas space 104 receives liquified gas from at least one liquified gas inlet 34. The liquified gas is then directed over or through weir 102 further towards the center of freezing section 20.

Referring back to FIG. 1, vessel 10 also includes microdroplet forming means 30, disposed in freezing section 20 at vessel top 14, for forming microdroplets 28 from a suitable solution. A microdroplet is defined herein as a drop of solution which, after freezing and subsequent extraction of the solution's solvent, will form a microparticle. Examples of suitable microdroplet forming means 30 include atomizers, nozzles and various gauge needles. Suitable atomizers include, for example, external air (or gas) atomizers (e.g., Model SUE15A; Spray Systems Co., Wheaton, Ill.), internal air atomizers (e.g., SU12; Spray Systems Co.), rotary atomizers (e.g., discs, bowls, cups and wheels; Niro, Inc., Columbia, Md.), and ultrasonic atomizers (e.g., Atomizing Probe 630-0434; Sonics & Materials, Inc., Danbury, Conn.). Suitable nozzles include pressure atomization nozzles (e.g, Type SSTC Whirl Jet Spray Drying Nozzles; Spray Systems Co., Wheaton, Ill.). Typical gauges of needles used to form microdroplets 28 include needles with gauges between about 16 and about 30.

In a preferred embodiment, microdroplet forming means 30 is an air atomizer, which can form microparticles 11 having a range of diameters between about 1 micrometer, or less, and about 300 micrometers. Average microparticle size can be changed by adjusting the pressure of the atomizing gas, supplied to an air atomizer (e.g., nitrogen gas). Increased gas pressure results in smaller average microparticle diameters.

Microdroplet forming means 30 is fabricated from a material, or combination of materials, which can withstand steam sanitizing and also the cold temperatures experienced in freezing section 20.

Microdroplet forming means 30 receives solution from at least one solution inlet 38. Solution inlet 38 provides fluid communication between solution source 40 and freezing section 20. It is understood that other suitable solution introduction means, such as a lance or an other device capable of injecting a solution into a cold environment, can be used in place of, or in combination with, solution inlet 38.

Vessel 10 also includes at least one three-phase port 42, which is disposed at internal wall 18, and provides fluid communication between freezing section 20 and extraction section 22. Three-phase port 42 is sized to allow the flow of a combination of frozen microdroplets 44, liquified gas and volatilized gas from freezing section 20 into extraction section 22.

Extraction section 22 includes means for separating a liquified gas from frozen microdroplets 44. In one embodiment, a suitable separating means comprises a means for heating extraction section 22, which then volatilizes the liquified gas, thus separating it from frozen microdroplets 44, usually contained within the lower portion of extraction section 22. Said heating means can also be used to warm the solvent frozen within frozen microdroplets 44. Suitable means for heating can include heat leakage from the outside environment, through side wall 12 and vessel bottom 16. Optionally, heating means can include, for example, electrical means such as heating coils, or recirculating heat exchanger tubes 46, through which a fluid can be circulated to control temperature within extraction section 22 to first volatilize the liquified gas, and then subsequently warm the solvent in frozen microdroplets 44 to control solvent extraction rate.

An alternate separating means comprises filtered bottom tap 48, which extends from the lower portion of extraction section 22. Filtered bottom tap 48, which contains filter 50, having a pore size less than the diameter of microparticles 11, typically $\leq 1$ micrometer, is suitable for removing liquids, such as liquified gas, from extraction section 22, while retaining frozen microdroplets 44, and possibly microparticles 11, within extraction section 22.

Gas outlet 52, which is disposed in extraction section 22 at internal wall 18, is suitable for directing gas, produced by volatilizing liquified gas, out of vessel 10. Gas outlet 52 can optionally include a means for reducing pressure within vessel 10, for example a vacuum blower (e.g., CP-21 low temperature blower, Barber Nichols, Arvada, Colo.) or vacuum pump (e.g. E2M18 vacuum pump, Edwards High Vacuum International, Crawley, West Sussex, England) suitable for impelling gases. Furthermore, gas outlet 52 typically includes filter 53 (e.g., a 0.2 micrometer sterile filter) in the gas flow path to support an aseptic process and provide assurance that formed microparticles 11 meet sterility requirements.

Vessel 10 can optionally include gas outlets 52, disposed in extraction section 22 and/or freezing section 20 (not shown). It is preferred that no gas outlets be disposed in freezing section 20, as gas venting out of freezing section 20 can result in gas circulation currents which can reduce the yield of microparticles 11 produced.

In addition, vessel 10 can optionally include at least one overpressure protection device (not shown), to protect the material integrity of vessel 10 from overpressurization caused by the volatilization of a liquified gas. Typical overpressure protection devices include, for instance, rupture disks or pressure relief valves.

Extraction section 22 also includes at least one non-solvent inlet 54, disposed at internal wall 18 and/or in side wall 12. Extraction section 22 receives a liquid non-solvent from non-solvent inlet 54 in a stream or spray. Preferably, non-solvent in extraction section 22 forms extraction bath 56, which is disposed in at least the lower portion of extraction section 22. Non-solvent inlet 54 provides fluid communication between cold non-solvent source 58 and extraction bath 56. It is understood that other suitable means, for introducing a liquid into a vessel under cold conditions, such as a lance or an other device capable of introducing a liquid under cold conditions, can be used in place of, or in combination with, non-solvent inlet 54.

In another embodiment, a suitable mixing means 60 for mixing frozen microdroplets 44 and non-solvent, is disposed in extraction bath 56. Mixing means 60 is provided to reduce the potential for formation of extraction gradients within extraction bath 56, such as could occur if frozen microdroplets 44 clumped at the bottom of extraction section 22. Examples of suitable mixing means 60 include low shear mixing devices, such as a turbine (e.g., Lightning Sealmaster P6X05E with an A310 impeller operating at about 0–175 rpm), a marine impeller, a paddle mixer or an external recirculation loop having a low shear pump.

Vessel 10 further includes bottom tap 62, which extends from the lower portion of extraction section 22. Bottom tap 62 is suitable for removing microparticles 11 and liquids, such as non-solvent, from vessel 10. Alternatively, dip tubes (not shown) may be used to remove microparticles 11 and liquids from vessel 10.

When required for drug delivery, relevant internal portions of the apparatus of this invention are cleaned and sanitized, or sterilized, between each use to assure the sterility of the final product.

In the method of this invention, microparticles of a material are formed from a solution of the material in a suitable solvent. Materials suitable for use in this method can include any soluble materials, provided a non-solvent is available which has a lower melting point than the solvent, and which has sufficient miscibility with the solvent to extract solid and/or thawed liquid solvent from a frozen microparticle. Preferably, materials used in this method include peptides, polypeptides, proteins, polymers, small molecule drugs and pro-drugs.

Any type of suitable polymer can also be used to form a microparticle. In a preferred embodiment, a polymer used in this method is biocompatible. A polymer is biocompatible if the polymer, and any degradation products of the polymer, such as metabolic products, are non-toxic to humans or animals, to whom the polymer was administered, and also present no significant deleterious or untoward effects on the recipient's body, such as an immunological reaction at the injection site. Biocompatible polymers can be biodegradable polymers, non-biodegradable polymers, a blend thereof or copolymers thereof.

Suitable biocompatible, non-biodegradable polymers include, for instance, polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, blends and copolymers thereof.

Suitable biocompatible, biodegradable polymers include, for example, poly(lactide)s, poly(glycolide)s, poly(lactide-co-glycolide)s, poly(lactic acid)s, poly(glycolic acid)s, polycarbonates, polyesteramides, polyanhydrides, poly(amino acids), polyorthoesters, polyacetals, polycyanoacrylates, polyetheresters, polycaprolactone, poly(dioxanone)s, poly(alkylene alkylate)s, polyurethanes, blends and copolymers thereof. Polymers comprising poly(lactides), copolymers of lactides and glycolides, blends thereof, or mixtures thereof are more preferred. Said polymers can be formed from monomers of a single isomeric type or a mixture of isomers.

A polymer used in this method can be blocked, unblocked or a blend of blocked and unblocked polymers. An unblocked polymer is as classically defined in the art, specifically having free carboxyl end groups. A blocked polymer is also as classically defined in the art, specifically having blocked carboxyl end groups. Generally, the blocking group is derived from the initiator of the polymerization reaction and is typically an alkyl radical.

Acceptable molecular weights for polymers used in this invention can be determined by a person of ordinary skill in the art taking into consideration factors such as the use of the microparticle, the desired polymer degradation rate, physical properties such as mechanical strength, and rate of dissolution of polymer in solvent. Typically, an acceptable range of molecular weights for polymeric microparticles having therapeutic uses is between about 2,000 Daltons to about 2,000,000 Daltons.

In an even more preferred embodiment, the polymer is a poly(lactide-co-glycolide) with a lactide:glycolide ratio of about 1:1 and a molecular weight of about 5,000 Daltons to about 70,000 Daltons. In an even more preferred embodiment, the molecular weight of the poly(lactide-co-glycolide) used in the present invention has a molecular weight of about 5,000 Daltons to about 42,000 Daltons.

Typically, a suitable polymer solution contains between about 1% (w/w) and about 30% (w/w) of a suitable biocompatible polymer, wherein the biocompatible polymer is typically dissolved in a suitable polymer solvent. Preferably, a polymer solution contains about 5% (w/w) to about 20% (w/w) polymer.

Microparticles can be formed by either a continuous freezing and extraction process or by a batch process wherein a batch of frozen microdroplets is formed in a first step, and then in a separate second step, the frozen microdroplets in the batch are extracted to form microparticles.

In this method, freezing zone 26 includes the portion of freezing section 20, which is substantially encircled by liquified gas flow 24. Freezing zone 26 is formed within freezing section 20 of vessel 10, by directing a flow 24 of a suitable liquified gas from at least two spray nozzles 32 in a substantially downward direction, toward side wall 12.

Typically, the liquified gas discharged from spray nozzles 32 is angled such that the liquified gas impinges against side wall 12 to form liquified gas flow 24 along the inside surface of side wall 12, thus wetting side wall 12. In a preferred embodiment, liquified gas, from each of six spray nozzles 32, is directed against side wall 12 at an angle to side wall 12 of less than about 30° to reduce the splashing or deflection of liquified gas off of side wall 12.

Alternately, liquified gas flow 24 is directed substantially parallel to, but displaced from the inside surface of side wall 12 to effectively form an independent wall of liquified gas extending from spray nozzles 32 to inner wall 18.

Liquified gas is provided to spray nozzles 32 from liquified gas source 36 through liquified gas inlet 34.

Liquified gases suitable for use in this method include liquid argon (−185.6° C.), liquid nitrogen (−195.8° C.), liquid helium or any other liquified gas having a temperature sufficiently low to freeze microdroplets 28 of a solution, while the microdroplets 28 are contained in freezing zone 26 or in liquified gas flow 24. Liquid nitrogen is preferred.

In an alternate embodiment, illustrated in FIG. 2, freezing zone 24 is formed within freezing section 20, by directing liquified gas from liquified gas source 36, through liquified gas inlet 34 and into liquified gas space 104, wherein the liquified gas then flows up over weir 102, or through slots (not shown) in weir 102 to form liquified gas flow 24. Liquified gas flow 24 then flows substantially downward along the inside surface of weir 102.

Referring back to FIG. 1, microdroplets 28 of a solution, preferably a solution of a polymer, are then directed through freezing zone 26, in a substantially downward direction, wherein microdroplets 28 freeze to form frozen microdroplets 44. A portion of microdroplets 28 may freeze by contacting liquified gas in liquified gas flow 24. Microdroplets 28 were previously formed by directing the solution from solution source 40, through solution inlet 38, into a suitable microdroplet forming means 30. Typically, within freezing section 20, at least a portion of the liquified gas will volatilize due to heat in-leakage and/or heat transfer from microdroplets 28 to the liquified gas.

A three-phase flow of volatilized gas, liquified gas and frozen microdroplets 44 then flows from the bottom of freezing section 20 and into extraction section 22, through three-phase port 42.

In one embodiment, at least a portion of frozen microdroplets 44 are entrained within liquified gas flow 24, which then carry frozen microdroplets 44 into extraction section 22. The entrainment of frozen microdroplets 44 within liquified gas flow 24 may improve the final yield of microparticles 11 produced, according to the method of invention, by transporting, into extraction section 22, frozen microdroplets 44 which might otherwise remain within freezing section 20, such as by adhering to side wall 12 and/or internal wall 18, and/or by reducing the loss of airborne frozen microdroplets 44 from vessel 10 through gas outlet 52.

The liquified gas is then separated from frozen microdroplets 44 by suitable separating means, leaving frozen microdroplets 44 disposed in the lower portion of extraction section 22.

In one embodiment, the liquified gas is heated to a temperature below the melting point of frozen microdroplets 44, but at or above the boiling point of the liquified gas whereby the liquified gas is vaporized and separated from frozen microdroplets 44.

Alternately, liquified gas can be separated by pulling a partial vacuum on extraction section 22 through gas outlet 52 and heating the liquified gas to a temperature below the boiling point of the liquified gas but high enough to elevate the vapor pressure of the liquified gas, thereby evaporating the liquified gas.

After heating, the liquified gas is volatilized, thereby separating the liquified gas from frozen microdroplets 44. The liquified gas can be heated by heat in-leakage from the outside environment through side wall 12 and vessel bottom 16. Preferably, extraction section 22 is heated by an electrical heat source or by recirculating a warmer fluid, such as nitrogen gas or a nitrogen gas/liquified nitrogen mixture, through heat exchanger tubes 46. In addition, a fluid can be circulated, through heat exchanger tubes 46, to control temperature within extraction section 22 to firstly volatilize the liquified gas in a controlled manner, and then subsequently to slowly warm the solvent in frozen microdroplets 44 to permit solvent extraction into the liquid non-solvent.

Alternately, liquified gas is separated from frozen microdroplets 44 by directing the liquified gas through filter 50 and then out of extraction section 22 through filtered bottom tap 48. Directing the liquified gas through filter 50 thereby removes the liquified gas from extraction section 22, while retaining frozen microdroplets 44 within the bottom portion of extraction section 22.

Wherein the liquified gas is separated by heating to volatilize the liquified gas, the resulting volatilized gas is then directed out of extraction section 22 through at least one gas outlet 52. Pressure within vessel 10 is primarily dependent upon the amount of liquified gas, which is volatilized within extraction section 22, and upon the discharge rate of gas through gas outlet 52. Vessel 10 can be operated at pressures above, equal to, or below atmospheric pressure. The upper pressure limit for performing this method is dependent upon the pressure rating of vessel 10.

It is preferred that the method of invention be performed, during formation of frozen microdroplets 44, under a partial vacuum. Achieving a partial vacuum within extraction section 22, and thus throughout vessel 10, is achieved by means known to one of skill in the art, such as using a pump or blower to take a suction through gas outlet 52 on extraction section 22.

Following separation of frozen microdroplets 44 from the liquified gas, frozen microdroplets 44 are then contacted with a suitable cold liquid non-solvent, which is at a temperature below the melting point of frozen microdroplets 44. In a preferred embodiment, the liquid non-solvent is maintained below the melting point of frozen microdroplets 44, and the solvent is extracted from the solid state into the liquid non-solvent to form porous microparticles 11 over a period of about 1 to about 24 hours. The extraction of solid state solvent slows the extraction process, thereby providing greater control of extraction and microparticle 11 formation.

In another embodiment, the liquid non-solvent is warmed to a temperature at or above the melting point of frozen microdroplets 44. The solvent in frozen microdroplets 44 thereby thaws and then, is extracted into the non-solvent. The solvent is thereby extracted as a solid and/or a liquid depending upon the various factors such as the volume of solvent in frozen microdroplet 44, the volume of non-solvent to which frozen microdroplet 44 is exposed, and the warming rate of frozen microdroplet 44. Depending upon the warming rate, the microparticle produced can also be porous, for lower warming rates, or significantly less porous due to partial particle condensation following rapid solvent extraction.

Non-solvent can be in the form of a spray, a stream and/or extraction bath 56. Preferably, frozen microdroplets 44 are immersed within the non-solvent of extraction bath 56.

Suitable non-solvents are defined as non-solvents of the material in solution, which are sufficiently miscible with the solvent of the solution to extract said solvent, out of the frozen microdroplets 44 as the solvent warms, thereby forming microparticles 11. In addition, the non-solvent has a melting point below the melting point of the frozen microdroplets 44.

In another embodiment, second non-solvents, such as hexane, are added to the first non-solvent, such as ethanol, to increase the rate of solvent extraction from certain polymers, such as poly(lactide-co-glycolidc).

In a preferred embodiment, at least a portion of frozen microdroplets 44 are entrained within the non-solvent, which may improve the final yield of microparticles 11 produced, according to the method of invention, by transporting frozen microdroplets 44 into extraction bath 56. The frozen microdroplets may otherwise have been lost in the process due to adhering to side wall 12, and/or from the loss of airborne frozen microdroplets 44 from vessel 10 through gas outlet 52.

In a further embodiment, frozen microdroplets 44 are then agitated within extraction bath 56 by mixing means 60 to reduce the concentration gradient of solvent within the non-solvent surrounding each frozen microdroplet 44 or microparticle 11, thereby improving the effectiveness of the extraction process.

In yet another embodiment, the extraction process includes the sequential addition to, and drainage of separate aliquots of non-solvent from, extraction section 22, to extract solvent into each separate aliquot. Extraction is thereby performed in a stepwise manner. Thawing rate is dependent on the choice of solvents and non-solvents, and the temperature of the non-solvent in extraction section 22. Table 1 provides exemplary polymer/solvent/non-solvent systems that can be used in this method along with their melting points.

TABLE 1

Appropriate Polymer Solvents and Non-Solvents Systems, with Solvent and Non-Solvent Melting Points

| POLYMER | SOLVENT (° C.) | NON-SOLVENT (° C.) |
|---|---|---|
| Poly(lactide) | Methylene Chloride (−95.1) | Ethanol (−114.5) |
| | Chloroform (−63.50) | Methanol (−97.5) |
| Poly(lactide-co-glyco-lide) | Ethyl Acetate (−83.6) | Ethanol (−114.5) |
| | Acetone (−95.4) | Ethyl ether (−116.3) |
| | Methylene Chloride (−95.1) | Pentane (−130) |
| | | Isopentane (−160) |
| Poly(capro-lactone) | Methylene Chloride (−95.1) | Ethanol (−114.5) |
| Poly(vinyl alcohol) | Water (0) | Acetone (−95.4) |
| Ethylene-vinyl acetate | Methylene Chloride (−95.1) | Ethanol (−114.5) |

For proteins it is preferred that frozen microdroplets 44 be slowly thawed while the polymer solvent is extracted to produce a microparticle.

A wide range of sizes of microspheres can be made by varying the droplet size, for example, by changing the nozzle diameter or air flow into an air atomizer. If very large diameters of microparticles 11 are desired, they can be extruded through a syringe directly into freezing zone 24. Increasing the inherent viscosity of the polymer solution can also result in an increasing microparticle size. The size of microparticles 11 produced by this process can range from greater than about 1000 down to about 1 micrometer, or less, in diameter. Usually, a microparticle will be of a size suitable for injection into a human or other animal. Preferably, the diameter of a microparticles 11 will be less than about 180 micrometers.

Following extraction, microparticles 11 are filtered and dried to remove non-solvent, by means known to one of skill in the art. For a polymeric microparticle, said microparticle is preferably not heated above its glass transition temperature to minimize adhesion between microparticles, unless additives, such as mannitol, are present to reduce adhesion between the microparticles.

In another embodiment, a solution of a material also contains one or more additional substance, which is dispersed within the solution. Said additional substance is dispersed by being co-dissolved in the solution, suspended as solid particles, such as lyophilized particles, within the solution, or dissolved in a second solvent, which is immiscible with the solution, and is mixed with the solution to form an emulsion. Solid particles, suspended in the solution can be large particles, with a diameter greater than 300 micrometers, or micronized particles with a diameter as small as about 1 micrometer. Typically, the additional substance should not be soluble in the non-solvent.

Wherein the material comprises a polymer, the polymer solution contains at least one biologically active agent. Examples of suitable therapeutic and/or prophylactic biologically active agents include proteins, such as immunoglobulin-like proteins; antibodies; cytokines (e.g., lymphokines, monokines and chemokines); interleukins; interferons; erythopoietin; hormones (e.g., growth hormone and adrenocorticotropic hormone); growth factors; nucleases; tumor necrosis factor; colony-stimulating factors; insulin; enzymes; antigens (e.g., bacterial and viral antigens); and tumor suppressor genes. Other examples of suitable therapeutic and/or prophylactic biologically active agents include nucleic acids, such as antisense molecules; and small molecules, such as antibiotics, steroids, decongestants, neuroactive agents, anesthetics, sedatives, cardiovascular agents, anti-tumor agents, antineoplastics, antihistamines, hormones (e.g., thyroxine) and vitamins.

Examples of suitable diagnostic and/or therapeutic biologically active agents include radioactive isotopes and radiopaque agents.

The microspheres made by this process can be either homogeneous or heterogeneous mixtures of the polymer and the active agent. Homogeneous mixtures are produced when the active agent and the polymer are both soluble in the solvent, as in the case of certain hydrophobic drugs such as steroids. Heterogeneous two phase systems having discrete zones of polymer and active agent are produced when the active agent is not soluble in the polymer/solvent, and is introduced as a suspension or emulsion in the polymer/solvent solution, as with hydrophilic materials such as proteins in methylene chloride.

The amount of a biologically active agent, which is contained in a specific batch of microparticles is a therapeutically, prophylactically or diagnostically effective amount, which can be determined by a person of ordinary skill in the art taking into consideration factors such as body weight, condition to be treated, type of polymer used, and release rate from the microparticle.

In one embodiment, a controlled release polymeric microparticle contains from about 0.01% (w/w) to approximately 50% (w/w) biologically active agent. The amount of the agent used will vary depending upon the desired effect of the agent, the planned release levels, and the time span over which the agent will be released. A preferred range of loading for biologically active agents is between about 0.1% (w/w) to about 30% (w/w).

When desired, other materials can be incorporated into microparticles with the biologically active agents. Examples of these materials are salts, metals, sugars, surface active agents. Additives, such as surface active agents, may also be added to the non-solvent during extraction of the solvent to reduce the possibility of aggregation of the microparticles.

The biologically active agent can also be mixed with other excipients, such as stabilizers, solubility agents and bulking agents. Stabilizers are added to maintain the potency of the agent over the duration of the agent's release. Suitable stabilizers include, for example, carbohydrates, amino acids, fatty acids and surfactants and are known to those skilled in the art. The amount of stabilizer used is based on ratio to the agent on a weight basis. For amino acids, fatty acids and carbohydrates, such as sucrose, lactose, mannitol, dextran and heparin, the molar ratio of carbohydrate to agent is typically between about 1:10 and about 20:1. For surfactants, such as the surfactants Tween™ and Pluronic™, the molar ratio of surfactant to agent is typically between about 1:1000 and about 1:20.

In another embodiment, a biologically active agent can be lyophilized with a metal cation component, to stabilize the agent and control the release rate of the biologically active agent from a microparticle, as described, in co-pending U.S. patent application Ser. No. 08/279,784, filed Jul. 25, 1994, the teachings of which are incorporated herein by reference.

Solubility agents are added to modify the solubility of the agent. Suitable solubility agents include complexing agents, such as albumin and protamine, which can be used to control the release rate of the agent from a polymeric or protein matrix. The weight ratio of solubility agent to biologically active agent is generally between about 1:99 and about 20:1.

Bulking agents typically comprise inert materials. Suitable bulking agents are known to those skilled in the art.

Further, a polymeric matrix can contain a dispersed metal cation component, to modulate the release of a biologically active agent from the polymeric matrix is described, in co-pending U.S. Pat. No. 5,656,297, filed May 3, 1994, to Bernstein et al. and in a co-pending International Application designating the United States, PCT/US95/05511, filed May 3, 1995, the teachings of which are incorporated herein by reference.

In yet another embodiment, at least one pore forming agent, such as a water soluble salt, sugar or amino acid, is included in the microparticle to modify the microstructure of the microparticle. The proportion of pore forming agent added to the polymer solution is between about 1% (w/w) to about 30% (w/w). It is preferred that at least one pore forming agent be included in a non-biodegradable polymeric matrix of the present invention.

Figure 3:
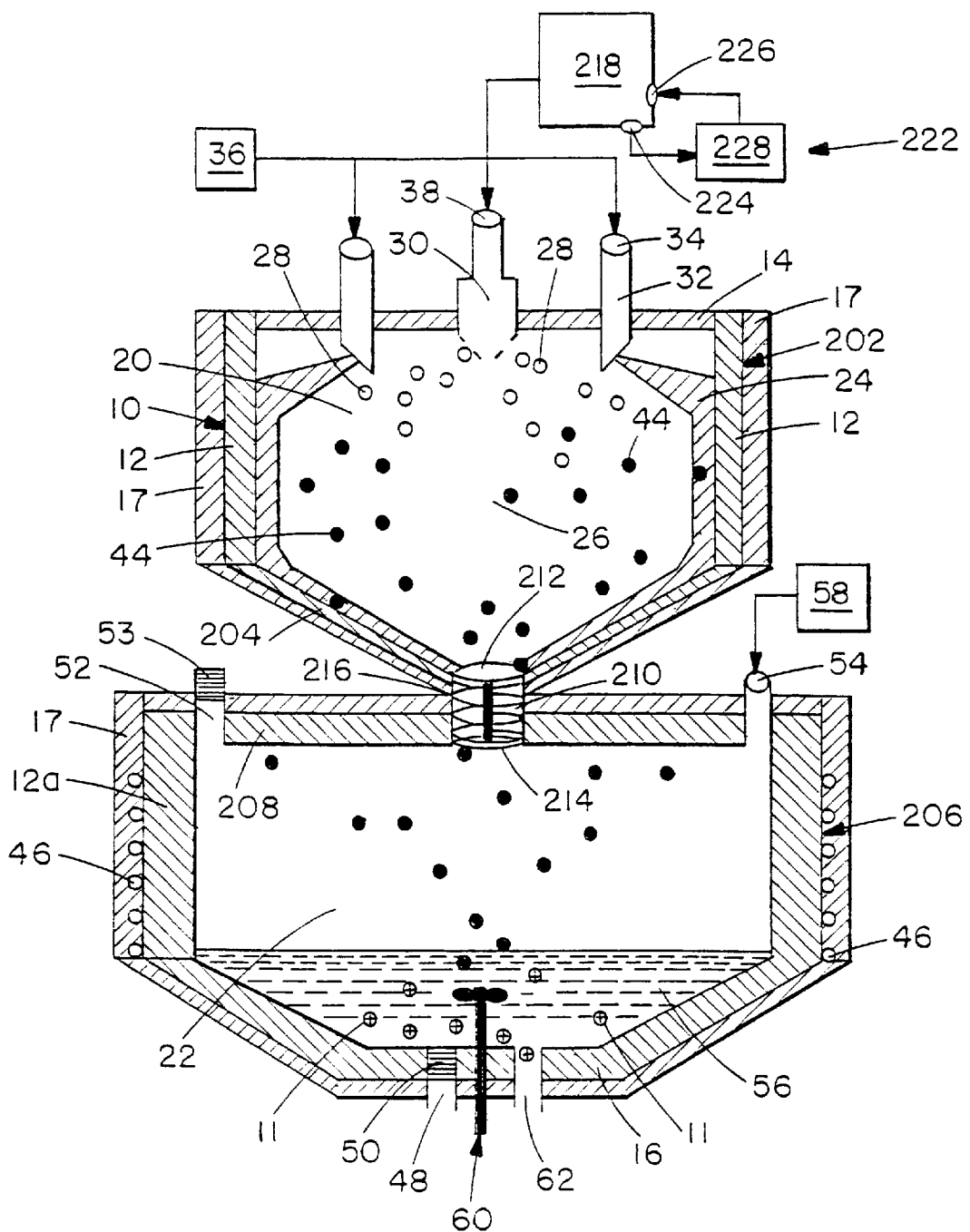
FIG. 3 is a cut-away side elevational illustration of yet another embodiment of an apparatus of the invention suitable for forming microparticles of a material according to the method of the invention, by freezing microdroplets of a solution of the material in a solvent, within a freezing zone cooled by an encircling flow of a liquified gas and then extracting the solvent from the frozen microdroplets, by exposure to a liquid non-solvent.

FIG. 3 illustrates yet another embodiment of an apparatus of the invention, suitable for performing the method of invention. The apparatus of FIG. 3 has many of the same elements of FIG. 1 and like elements are designated with like numerals. In this apparatus, freezing section 20 is disposed within freezing vessel 202, and is substantially enclosed by side wall 12, vessel top 14 and freezing vessel bottom 204. Extraction section 22 is disposed, likewise, within extraction vessel 206, and is substantially enclosed by, side wall 12a, extraction vessel top 208 and vessel bottom 16. Freezing vessel 202 is disposed generally above extraction vessel 206. Conduit 210 is disposed between freezing vessel 202 and extraction vessel 206. Conduit 210 includes conduit inlet 212, disposed at or near freezing vessel bottom 204, and conduit outlet 214, disposed at or near extraction vessel top 208. Conduit 210 provides three-phase communication, specifically solids, liquids and gases, between freezing section 20 and extraction section 22.

Optionally, conduit 210 includes three-phase mixing means 216 for mixing the three phases in the three-phase flow, whereby at least a portion of frozen microdroplets 44 contained in the gaseous phase will be captured in the liquid phase, thereby increasing product yield by reducing the loss of frozen microdroplets 44 from venting gases through gas outlet 52. Suitable three-phase mixing means 216 include a cascading baffle, or preferably, one or more elements of a static mixer (e.g., Model# KMR-SAN; Chemineer, Inc.). A preferred three-phase mixing means 216 provides a tortuous flow. More preferably, three-phase mixing means 216 comprises a number of in-series static mixer elements sufficient to create turbulent flow, typically four elements.

In a further embodiment, solution source 40, includes mix tank 218, having a second mixing means (not shown) and fragmentation loop 222. Any means for mixing a solution, suspension or emulsion is suitable for a second mixing means. High shear mixing is preferred for the second mixing means.

Fragmentation loop 222 includes fragmentation inlet 224, which is disposed at, or near, the bottom of dispersion tank 218, fragmentation outlet 226, which is disposed at dispersion tank 218 generally elevated above fragmentation inlet 224. Fragmentation loop 222 also includes fragmentation means 228, which is disposed between fragmentation inlet 224 and fragmentation outlet 226, and which reduces, or micronizes the size of particles suspended in the material solution; and which forms finer, better blended, emulsions of immiscible liquids. Suitable fragmentation means 228 include means capable of fragmenting a solid to a diameter between about 1 micrometer, or less, and about 10 micrometers. Examples of suitable fragmentation means 228 include rotor/stator homogenizers, colloid mills, ball mills, sand mills, media mills, high pressure homogenizers.

In an alternate embodiment, fragmentation occurs within mix tank 218 by the use of disruptive energy, such as that provided by a sonic probe, high shear mixer or homogenizer.

The temperature of dispersion tank 218 and/or of fragmentation loop 222 is typically controlled when containing proteins, or other heat sensitive materials, by means known in the art, to minimize protein denaturing.

In a method illustrated in FIG. 3, the volatilized gas, liquified gas and frozen microdroplets 44 are directed from freezing section 20 and through conduit 210, which includes three-phase mixing means 216, preferably a four-element, or more, static mixer, to turbulently mix the three phases and scrub frozen microdroplets 44, which were entrained in the gas phase, into the liquified gas, thereby improving yield.

In another embodiment, a solution containing an additional substance, which is in solid form or which forms an emulsion with the solvent, is recirculated through fragmentation means 228, such as a homogenizer, to micronize the solid particles, preferably particulates of about 1–10 micrometers in diameter, or to further blend the emulsion to form smaller emulsion droplets.

Fragmentation is not required when the solution has no suspended particles, or when larger suspended particles are desired.

Alternately, the second mixing means can be used as a fragmentation means, such as when a high speed/high shear mixer is used for the second mixing means.

Figure 4:
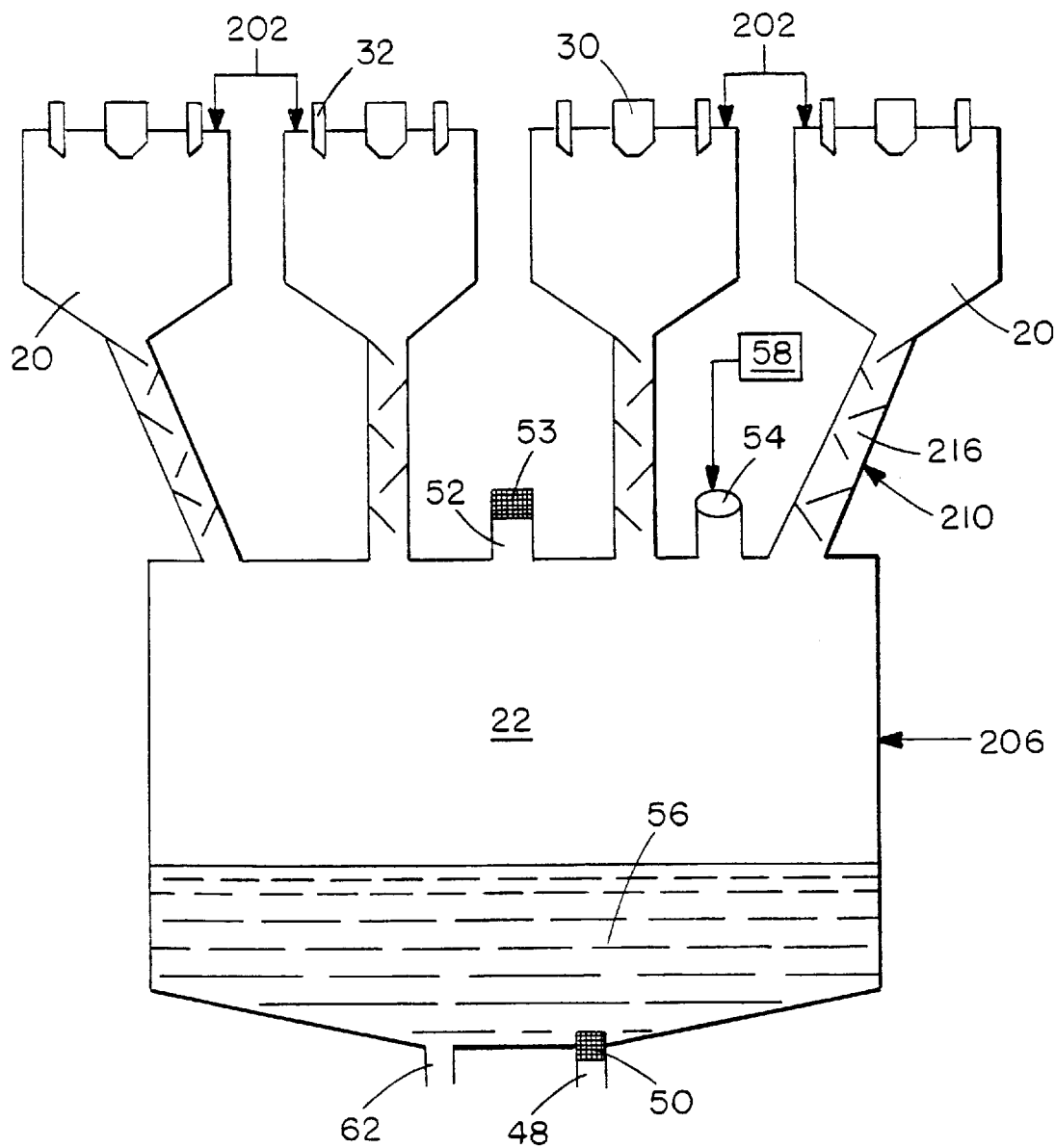
FIG. 4 is a cut-away side elevational illustration of an alternate embodiment of an apparatus of the invention suitable for forming microparticles of a material according to the method of the invention, by freezing microdroplets of a solution of the material in a solvent, within a freezing zone cooled by an encircling flow of a liquified gas and then extracting the solvent from the frozen microdroplets, by exposure to a liquid non-solvent.

FIG. 4 illustrates yet another embodiment of an apparatus of the invention, suitable for performing the method of invention. The apparatus of FIG. 4 has many of the same elements of FIGS. 1 and 3, and like elements are designated with like numerals. This apparatus includes multiple freezing vessels 202, each containing a separate freezing section 20. The apparatus also includes one extraction vessel 206, having extraction section 22. Three-phase communication is provided from each freezing section 20 to extraction section 22 by separate conduits 210. Each conduit 210 includes separate three-phase mixing means 216.

In the method illustrated in FIG. 4, frozen microdroplets 44 are formed in each freezing section and then transferred to a common extraction section 22.

The composition made according to the method of this invention can be administered to a human, or other animal, orally, by suppository, by injection or implantation subcutaneously, intramuscularly, intraperitoneally, intracranially, and intradermally, by administration to mucosal membranes, such as intranasally or by means of a suppository, or by in situ delivery (e.g. by enema or aerosol spray) to provide the desired dosage of a biologically active agent based on the known parameters for treatment of various medical conditions.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method for forming microparticles of a material from microdroplets of a solution of the material and a solvent, comprising the steps of:

a) directing the microdroplets into a freezing section containing a liquefied gas, whereby the microdroplets freeze; and b) contacting the frozen microdroplets in an extraction section with a liquid non-solvent to extract the solvent into the non-solvent thereby forming said microparticles; wherein the freezing section and extraction section are separated, the non-solvent is in the liquid state throughout the method and the material comprises a biocompatible polymer.

2. The method of claim 1 wherein the material further comprises a biologically active agent.

3. The method of claim 2 wherein said biologically active agent is selected from the group consisting of immunoglobulin proteins, interleukins, interferons, erythropoietin, antibodies, cytokines, hormones, antigens, growth factors, nucleases, tumor enzymes, tumor suppression genes, antisense molecules, antibiotics, anesthetics, sedatives, cardiovascular agents, antitumor agents, antineoplastics, antihistamines and vitamins.

4. The method of claim 1 wherein the biocompatible polymer is biodegradable.

5. The method of claim 4 wherein said biocompatible and biodegradable polymer is selected from the group consisting of poly(lactide)s, poly(glycolide)s, poly(lactide-co-glycolide)s, poly(lactic acid)s, poly(glycolic acid)s, polycarbonates, polyesteramides, polyanhydrides, poly (amino acids), polyorthoesters, polyacetals, polycyanoacrylates, polyetheresters, polycaprolactone, poly (dioxanone)s, poly(alkylene alkylate)s, polyurethanes, blends and copolymers thereof.

6. The method of claim 4 wherein the material further comprises a biologically active agent.

7. The method of claim 6 wherein the biologically active agent is a protein.

8. The method of claim 1 wherein the temperature of step (a) is lower than the temperature of step (b).

9. The method of claim 1 wherein the liquefied gas is sprayed into the freezing section.

10. The method of claim 1 wherein the microdroplets are formed by atomizing the solution of the material into the freezing section.

11. The method of claim 1 wherein the frozen microdroplets are collected at the bottom of the freezing section and directed into the extraction section.

12. A method for forming microparticles of a material from microdroplets of a solution of the material and a solvent, comprising the steps of:
 a) directing the microdroplets into a freezing vessel containing a liquefied gas, whereby the microdroplets freeze; and
 b) contacting the frozen microdroplets in an extraction vessel with a liquid non-solvent to extract the solvent into the non-solvent thereby forming said microparticles; wherein the freezing vessel and extraction vessel are separated, the non-solvent is in the liquid state throughout the method and the material comprises a biocompatible polymer.

13. The method of claim 12 wherein the material further comprises a biologically active agent.

14. The method of claim 13 wherein said biologically active agent is selected from the group consisting of immunoglobulin proteins, interleukins, interferons, erythropoietin, antibodies, cytokines, hormones, antigens, growth factors, nucleases, tumor enzymes, tumor suppression genes, antisense molecules, antibiotics, anesthetics, sedatives, cardiovascular agents, antitumor agents, antineoplastics, antihistamines and vitamins.

15. The method of claim 12 wherein the biocompatible polymer is biodegradable.

16. The method of claim 15 wherein said biocompatible and biodegradable polymer is selected from the group consisting of poly(lactide)s, poly(glycolide)s, poly(lactide-co-glycolide)s, poly(lactic acid)s, poly(glycolic acid)s, polycarbonates, polyesteramides, polyanhydrides, poly(amino acids), polyorthoesters, polyaetals, polycyanoacrylates, polyetheresters, polycaprolactone, poly(dioxanone)s, poly(alkylene alkylate)s, polyurethanes, blends and copolymers thereof.

17. The method of claim 15 wherein the material further comprises a biologically active agent.

18. The method of claim 17 wherein the biologically active agent is a protein.

19. The method of claim 12 wherein the temperature of step (a) is lower than the temperature of step (b).

20. The method of claim 12 wherein the liquefied gas is sprayed into the freezing vessel.

21. The method of claim 12 wherein the microdroplets are formed by atomizing the solution of the material into the freezing vessel.

22. The method of claim 12 wherein the frozen microdroplets are collected at the bottom of the freezing vessel and directed into the extraction vessel.

* * * * *